(12) United States Patent
McDermott et al.

(10) Patent No.: US 6,248,919 B1
(45) Date of Patent: Jun. 19, 2001

(54) PROCESS FOR THE PREPARATION OF FARNESYLTRANSFERASE INHIBITORS

(75) Inventors: Todd S. McDermott, Oak Park; Anne E. Bailey, Waukegan; Ramiya Premchandran, Gurnee; Lakshima Bhagavatula, Vernon Hills, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/410,956

(22) Filed: Oct. 5, 1999

(51) Int. Cl.$^7$ .................................................. C07L 229/00
(52) U.S. Cl. ............................ 560/41; 560/102; 562/450; 562/492; 562/856
(58) Field of Search ...................... 560/41, 102; 562/450, 562/492, 856

(56) References Cited

FOREIGN PATENT DOCUMENTS

WO 9850029 * 11/1998 (WO).

OTHER PUBLICATIONS

Doyle, Michael P., et al., Alkyl Nitrite–Metal Halide Deamination Reactions.6. Direct Synthesis of Arenediazonium Tetrafluoroborate Salts from Aromatic Amines, tert–butyl Nitrite, and Boron Trifluoride Etherate in Anhydrous Media, Journal of Organic Chemistry, vol. 44, No. 9, 1572–1574 (1979).

Darses, Sylvain, et al., "Cross–Coupling of Arenediazonium Tetrafluoroborates with Arylboronic Acids Catalysed by Palladium", Tetrahedron Letters, vol. 37, No. 22, pp. 3857–3860 (1996).

* cited by examiner

Primary Examiner—Paul J. Killos
(74) Attorney, Agent, or Firm—Gregory W. Steele; B. Gregory Donner

(57) ABSTRACT

A process for the preparation of preparation of farnesyltransferase inhibitors of formula (I)

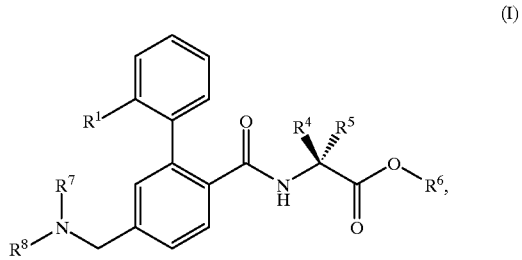

or pharmaceutically acceptable salts or prodrugs thereof, is disclosed.

17 Claims, No Drawings

PROCESS FOR THE PREPARATION OF FARNESYLTRANSFERASE INHIBITORS

TECHNICAL FIELD

The instant invention relates to a process for the preparation of farnesyltransferase inhibitors.

BACKGROUND OF THE INVENTION

Ras oncogenes are the most frequently identified activated oncogenes in human tumors. Transformed protein Ras is involved in the proliferation of cancer cells. Ras must be farnesylated before this proliferation can occur. Farnesylation of Ras by farnesyl pyrophosphate is effected by farnesyltransferase. Inhibition of farnesyltransferase and, thereby, of farnesylation of the Ras protein, blocks the ability of transformed cells to proliferate. Therefore, there is a need for compounds which are inhibitors of farnesyltransferase.

The large scale production of farnesyltransferase inhibitors requires chemical syntheses which avoid complicating factors such as use of high cost reagents, chemicals which require special handling, lengthy multi-step synthetic sequences, chromatography of intermediates, and low-yielding steps. An effective strategy to lower the cost associated with multi-step processes is the reduction in the number of steps required to complete the synthesis by combining several steps into a "single pot," thereby forming a continuous process. However, running multiple steps in a single reaction vessel or without purification of intermediates poses a challenge due to competing side reactions, solvent incompatibilities, and purification difficulties.

The instant invention discloses a novel synthesis of farnesyltransferase inhibitors which allows multiple reaction steps in a single reaction vessel without isolation of intermediates. In addition, this invention provides a process that avoids costly chromatography of the intermediates and products.

SUMMARY OF THE INVENTION

In its principle embodiment, the instant invention discloses a process for preparing a compound of structural formula (I)

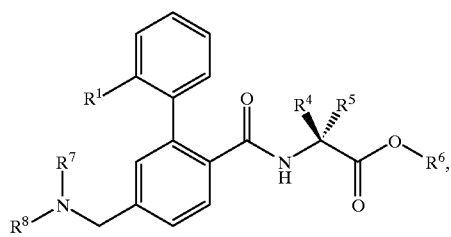

(I)

or a pharmaceutically acceptable salt or prodrug thereof, wherein $R^1$ is methyl, ethyl, propyl, iso-propyl, halo, or haloalkyl;
one of $R^4$ or $R^5$ is hydrogen or alkyl, and the other is alkenyl, alkoxyalkyl, alkoxyarylalkyl, alkoxycarbonylalkyl, alkylsulfinylalkyl, alkylsulfonylalkyl, alkyl, alkynyl, aminoalkyl, aminocarbonylalkyl, aminothiocarbonylalkyl, aryl, arylalkyl, carboxyalkyl, cyanoalkyl, cycloalkylalkoxyalkyl, cycloalkyl, cycloalkylalkyl, cycloalkylsulfinylalkyl, cycloalkylsulfonylalkyl, (heterocycle)alkyl, hydroxyalkyl, hydroxyarylalkyl, sulfhydrylalkyl, thioalkoxyalkyl optionally substituted with one, two, or three halo substituents, or thiocycloalkoxyalkyl;

$R^6$ is hydrogen or a carboxy protecting group; and
$R^7$ and $R^8$ are independently hydrogen, alkenyl, alkyl, alkynyl, aryl, arylalkyl, cycloalkyl, cycloalkylalkyl, heterocycle, or (heterocycle)alkyl;
wherein, at each occurence, the aryl and the heterocycle can be optionally substituted with one, two, three, four, or five substituents independently selected from alkenyl, alkyl, alkynyl, aryl, arylalkyl, cycloalkyl, cycloalkylalkyl, heterocycle, (heterocycle)alkyl, carboxaldehyde, azido, nitro, amino, cyano, hydroxy, sulfhydryl, and —$L^1$—$R^6$,
wherein $L^1$ is —C(X)—, —S(O)$_t$—, —NR$^{12}$—, —O—, —X'C(X)—, —C(X)X'—, —N(R$^{12}$)C(O)N(R$^{12}$)—, —N(R$^{12}$)C(X)—, —C(X)N(R$^{12}$)—, —NR$^{12}$S(O)$_t$—, or —S(O)$_t$NR$^{12}$—; and
wherein $R^6$ and $R^{12}$ are independently hydrogen, alkenyl, alkyl, alkynyl, aryl, arylalkyl, cycloalkyl, cycloalkylalkyl, heterocycle, or (heterocycle)alkyl; and
wherein X and X' are independently O or S, and
wherein t is zero, one, or two,
the process comprising,
(a) reacting a compound of structural formula

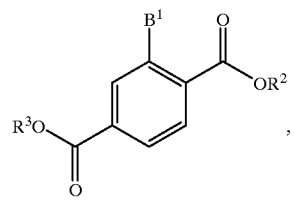

wherein $B^1$ is diazonium tetrafluoroborate, chloride, bromide, iodide, methylsulfonate, or trifluoromethylsulfonate; and $R^2$ and $R^3$ are independently alkyl, arylalkyl, cycloalkyl, or haloalkyl with a compound of structural formula

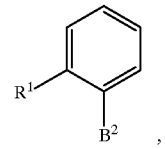

wherein $R^1$ is defined above, and $B^2$ is —Sn(alkyl)$_3$, or —B(OR$^9$)(OR$^{10}$), wherein $R^9$ and $R^{10}$ are hydrogen or alkyl, or $R^{10}$ and $R^{11}$, together with the oxygen atoms to which they are attached, are alkylene, wherein the alkylene can be optionally substituted with one, two, three, or four alkyl substituents, in the presence of a catalyst and a first base, to provide a first intermediate of structural formula

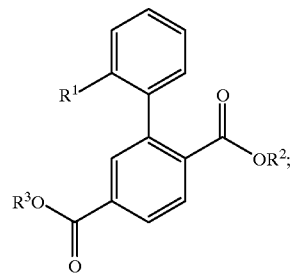

(b) reacting the first intermediate with a second base in a second solvent system, the second solvent system comprising water and an organic component, to provide a second intermediate of structural formula

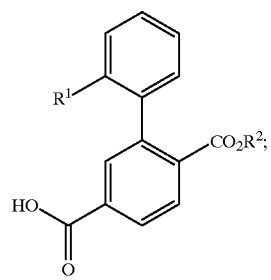

(c) reacting the second intermediate with a reducing agent to provide a third intermediate of structural formula

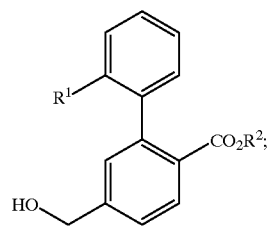

(d) reacting the third intermediate with a hydrolyzing agent to provide a fourth intermediate of structural formula

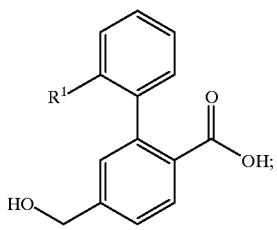

(e) reacting the fourth intermediate compound with first halogenating agent to provide a fifth intermediate of structural formula

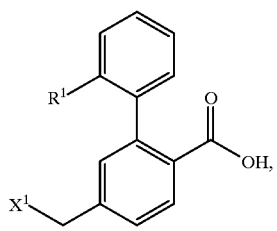

wherein $X^1$ is halo;

(f) reacting the fifth intermediate compound with a second halogenating agent to provide a sixth intermediate of structural formula

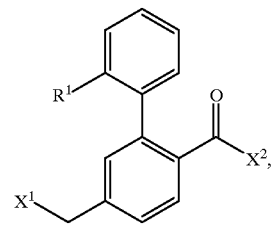

wherein $X^2$ is halo;

(g) reacting the sixth intermediate with a compound of structural formula

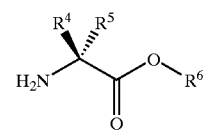

in the presence of a third base to provide a seventh intermediate of structural formula

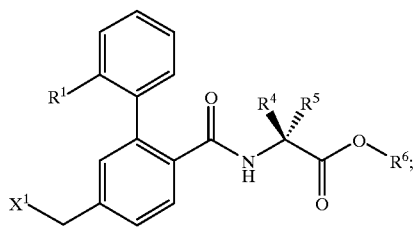

(h) reacting the seventh intermediate with $HN(R^7)(R^8)$ in the presence of the third base to provide the compound of structural formula (I), wherein $R^6$ is a carboxy-protecting group; and (i) reacting the compound of formula (I) with the second base to provide the compound of structural formula (I), wherein $R^6$ is hydrogen.

In another embodiment of the instant invention is disclosed a process for preparing (2S)-2-(((5-((butyl(2-cyclohexylethyl)amino)methyl)-2'-methyl(1,1'-biphenyl)-2-yl)carbonyl)amino)-4-(methylsulfanyl)butanoic acid, or a pharmaceutically acceptable salt or prodrug thereof.

In yet another embodiment of the instant invention is disclosed a process for preparing a compound of structural formula (II)

(II)

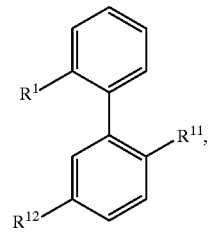

wherein
$R^1$ is methyl, ethyl, propyl, iso-propyl, halo, or haloalkyl;
$R^{11}$ is carboxy, halocarbonyl, or alkoxycarbonyl, wherein the alkoxycarbonyl can be optionally substituted with cycloalkyl, aryl, or halo; and $R^{12}$ is alkoxycarbonyl, wherein the alkoxycarbonyl can be optionally substituted with cycloalkyl, aryl, or halo, carboxy, hydroxymethyl, halomethyl, or —$CH_2OSO_2R^4$, wherein $R^4$ is alkyl, haloalkyl, or phenyl, wherein the phenyl can be optionally substituted with one, two, or three substituents independently selected from halo, nitro, alkyl, or haloalkyl, the process comprising:

(a) reacting a compound of structural formula

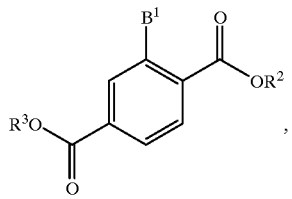

wherein $B^1$ is diazonium tetrafluoroborate, chloride, bromide, iodide, methylsulfonate, or trifluoromethylsulfonate; and $R^2$ and $R^3$ are independently alkyl, arylalkyl, cycloalkyl, or haloalkyl with a compound of structural formula

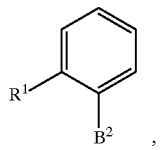

wherein $R^1$ is defined above, and $B^2$ is —$Sn(alkyl)_3$, or —$B(OR^9)(OR^{10})$, wherein $R^9$ and $R^{10}$ are hydrogen or alkyl, or $R^{10}$ and $R^{11}$, together with the oxygen atoms to which they are attached, are alkylene, wherein the alkylene can be optionally substituted with one, two, three, or four alkyl substituents, in the presence of a catalyst and a first base, to provide a first intermediate of structural formula

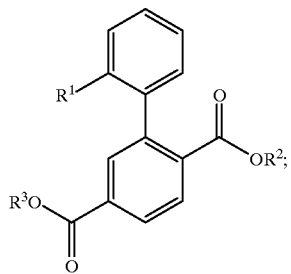

(b) optionally reacting the first intermediate with a second base in a second solvent system, the second solvent system comprising water and an organic component, to provide a second intermediate of structural formula

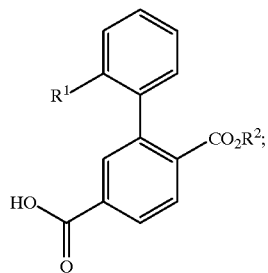

(c) optionally reacting the second intermediate with a reducing agent to provide a third intermediate of structural formula

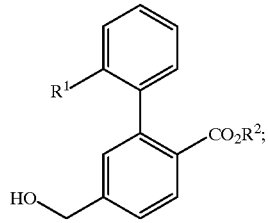

(d) optionally reacting the third intermediate with a hydrolyzing agent to provide a fourth intermediate of structural formula

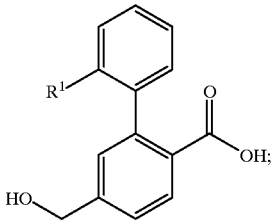

(e) optionally reacting the fourth intermediate compound with an activating agent optionally in the presence of a third base to provide a fifth intermediate of structural formula

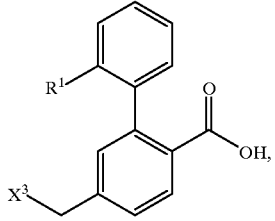

wherein $X^3$ is halo or —$OSO_2R^4$;

(f) optionally reacting the fifth intermediate compound with a second halogenating agent to provide a sixth intermediate of structural formula

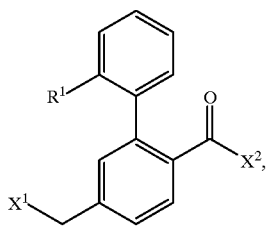

wherein $X^2$ is halo.

In still yet another embodiment of the instant invention are disclosed compounds of structural formula (II)

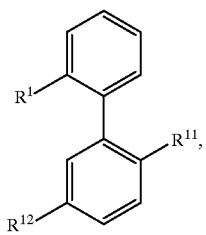

(II)

wherein
$R^1$ is methyl, ethyl, propyl, iso-propyl, halo, or haloalkyl;
$R^{11}$ is carboxy, halocarbonyl, or alkoxycarbonyl, wherein the alkoxycarbonyl can be optionally substituted with cycloalkyl, aryl, or halo; and
$R^{12}$ is alkoxycarbonyl, wherein the alkoxycarbonyl can be optionally substituted with cycloalkyl, aryl, or halo, carboxy, hydroxymethyl, halomethyl, or —$CH_2OSO_2R^4$, wherein $R^4$ is alkyl, haloalkyl, or phenyl, wherein the phenyl can be optionally substituted with one, two, or three substituents independently selected from halo, nitro, alkyl, or haloalkyl.

DETAILED DESCRIPTION OF THE INVENTION

When yields of compounds in solution are are reported, the amount of compound in those solutions is calculated based on comparison with known HPLC standards. Percentages obtained by HPLC analysis are defined by peak area calculations.

As used in the specification and the claims, the following terms have the meanings specified:

The term "activating agent," as used herein, refers to first halogenating agents or sulfonating agents.

The term "alkenyl," as used herein, refers to a monovalent straight or branched chain hydrocarbon having two to six carbon atoms and at least one carbon-carbon double bond.

The term "alkyl," as used herein, refers to a monovalent straight or branched chain saturated hydrocarbon having one to six carbon atoms.

The term "alkylene," as used herein, refers to a divalent straight or branched chain saturated hydrocarbon having one to six carbon atoms.

The term "alkynyl," as used herein, refers to a monovalent straight or branched chain hydrocarbon having two to six carbon atoms and at least one carbon-carbon triple bond.

The term "amino," as used herein, refers to —$NH_2$ or a derivative thereof formed by independent replacement of one or both hydrogens thereof by a group selected from alkyl, aryl, arylalkyl, cycloalkyl, or cycloalkylalkyl.

The term "aminoalkyl," as used herein, refers to an alkyl group to which is attached at least one amino group.

The term "aminocarbonyl," as used herein, refers to an amide; i.e., an amino group attached to the parent molecular group through a carbonyl.

The term "aminocarbonylalkyl," as used herein, refers to an alkyl group to which is attached at least one aminocarbonyl group.

The term "aminothiocarbonyl," as used herein, refers to a thioamide; i.e., an amino group attached to the parent molecular group through a thiocarbonyl.

The term "aminothiocarbonylalkyl," as used herein, refers to an alkyl group to which is attached at least one aminothiocarbonyl group.

The term "alkoxy," as used herein, refers to an alkyl group connected to the parent molecular group through an oxygen atom.

The term "alkoxyalkyl," as used herein, refers to an alkyl group to which is attached at least one alkoxy group.

The term "alkoxycarbonyl," as used herein, refers to an ester group; i.e. an alkoxy group attached to the parent molecular group through a carbonyl. The alkoxycarbonyl groups of this invention can be optionally substituted.

The term "alkoxycarbonylalkyl," as used herein, refers to an alkyl group to which is attached at least one alkoxycarbonyl group.

The term "alkoxyaryl," as used herein, refers to an aryl group to which is attached at least one alkoxy group.

The term "alkoxyarylalkyl," as used herein, refers to an alkyl group to which is attached at least one alkoxyaryl group.

The term "aryl," as used herein, refers to a mono- or bicyclic carbocyclic ring system having at least one aromatic ring and is exemplified by phenyl, naphthyl, 1,2-dihydronaphthyl, 1,2,3,4-tetrahydronaphthyl, fluorenyl, indanyl, and indenyl. The aryl groups of this invention can be optionally substituted.

The term "arylalkyl," as used herein, refers to an alkyl group to which is attached at least one aryl group.

The term "alkylsulfinyl," as used herein, refers to an alkyl group attached to the parent molecular group through a sulfoxide.

The term "alkylsulfinylalkyl," as used herein, refers to an alkyl group to which is attached at least one alkylsulfinyl group.

The term "alkylsulfonyl," as used herein, refers to an alkyl group attached to the parent molecular group through a sulfone.

The term "alkylsulfonylalkyl," as used herein, refers to an alkyl group to which is attached at least one alkylsulfonyl group.

The term "azido," as used herein, refers to —$N_3$.

The term "carbonyl," as used herein, refers to —C(=O)—.

The term "carboxaldehyde," as used herein, refers to —CHO.

The term "carboxy," as used herein, refers to —$CO_2H$.

The term "carboxy-protecting group," as used herein, refers to a carboxylic acid protecting ester group employed to block or protect carboxylic acid functionality while reactions involving other functional sites of the molecule are performed. Carboxy-protecting groups are disclosed in T. H. Greene and P. G. M. Wuts, *Protective Groups in Organic*

*Synthesis*, 2nd edition, John Wiley & Sons, New York (1991). A carboxy-protecting group can also be used as a prodrug whereby the carboxy-protecting group can be readily cleaved in vivo such as, for example, by enzymatic hydrolysis in blood, to release the biologically active parent. Such carboxy-protecting groups are well-known to those skilled in the art, having been extensively used in the protection of carboxyl groups in the penicillin and cephalosporin fields as described in U.S. Pat. No. 3,840,556 and U.S. Pat. No. 3,719,667. Examples of esters useful as prodrugs for compounds containing carboxyl groups can be found on pages 14–21 of "Bioreversible Carriers in Drug Design: Theory and Application," edited by E. B. Roche, Pergamon Press, New York (1987). Representative carboxy-protecting groups are alkyl groups such as methyl, ethyl, and tertiary butyl; benzyl groups and substituted derivatives thereof such as alkoxybenzyl or nitrobenzyl; dialkylaminoalkyl groups such as dimethylaminoethyl; alkylcarbonylalkyl groups such as pivaloyloxymethyl or propionyloxymethyl; aryloxyalkyl groups such as benzoyloxyethyl; alkoxycarbonylalkyl groups such as methoxycarbonylmethyl and cyclohexyloxycarbonylmethyl; alkoxycarbonyloxyalkyl groups such as tertiarybutyloxycarbonyloxymethyl; alkoxycarbonylarninoalkyl groups such as tertiary- butyloxycarbonylaminomethyl; alkylaminocarbonylaminoalkyl groups such as methylaminocarbonylaminomethyl; alkanoylaminoalkyl groups such as acetylarninomethyl; (heterocyclic)carbonyloxyalkyl groups such as 4-methylpiperazinyl-carbonyloxymethyl; and dialkylaminocarbonylalkyl groups such as dimethylaminocarbonylmethyl.

The term "carboxyalkyl," as used herein, refers to an alkyl group to which is attached at least one carboxy group.

The term "catalyst," as used herein, refers to palladium (Pd) complexes useful for enhancing the rates of biaryl couplings such as those summarized in step (a). Examples of catalysts include tetrakis(triphenylphosphine)palladium(0), palladium(II) acetate, Pd$_2$Cl$_2$(dba), and PdCl$_2$.CH$_2$Cl$_2$. Each of the aformentioned catalysts can be used with triphenylphosphine, triphenylarsine, or a trialkylphosphine such as tributylphosphine optionally present.

The term "cyano," as used herein, refers to —CN.

The term "cyanoalkyl," as used herein, refers to an alkyl group to which is attached at least one cyano group.

The term "cycloalkylalkoxy," as used herein, refers to an alkoxy group to which is attached a cycloalkyl group.

The term "cycloalkylalkoxyalkyl," as used herein, refers to an alkyl group to which is attached at least one cycloalkylalkoxy group.

The term "cycloalkyl," as used herein, refers to a monovalent saturated cyclic or bicyclic hydrocarbon having three to twelve carbon atoms.

The term "cycloalkylalkyl," as used herein, refers to an alkyl group to which is attached at least one cycloalkyl group.

The term "cycloalkylsulfinyl," as used herein, refers to a cycloalkyl group attached to the parent molecular group through a sulfoxide.

The term "cycloalkylsulfinylalkyl," as used herein, refers to an alkyl group to which is attached at least one cycloalkylsulfinyl group.

The term "cycloalkylsulfonyl," as used herein, refers to cycloalkyl group attached to the parent molecular group through a sulfone.

The term "cycloalkylsulfonylalkyl," as used herein, refers to an alkyl group to which is attached at least one cycloalkylsulfonyl group.

The term "diazonium tetrafluoroborate," as used herein, refers to —[N$_2$]$^+$[BF$_4$]$^-$.

The term "first base," as used herein, refers to compounds capable of accepting protons which are useful for promoting biaryl couplings such as those summarized in step (a). Examples of first bases include carbonates such as potassium carbonate, potassium bicarbonate sodium carbonate, and sodium bicarbonate; halides such as cesium fluoride; and phosphates such as potassium phosphate, potassium dihydrogen phosphate, or potassium hydrogen phosphate.

The term "first halogenating agent," as used herein, refers to reagents or combinations of reagents useful for the conversion of benzyl alcohol groups to benzyl halide groups such as those summarized in step (e). Examples of first halogenating agents include a mixture of N-bromosuccinimide and triphenylphosphine, a mixture of carbon tetrabromide and triphenylphosphine, a mixture of tribromomethane and triphenylphosphine, a mixture of lithium bromide and triphenylphosphine, phosphorus tribromide a mixture of phosphorus tribromide and lithium bromide, and hydrobromic acid.

The terms "halo" or "halide" as used herein, refer to F, Cl, Br, or I.

The term "haloalkyl," as used herein, refers to an alkyl group to which is attached at least one halo group. The term "haloalkyl," as used herein, also refers to perfluoroalkyl or perchloroalkyl.

The term "halocarbonyl," as used herein, refers to an acid halide; i.e. a halide attached to the parent molecular group through a carbonyl.

The term "heterocycle," as used herein, refers to a five-, six-or seven-membered saturated or unsaturated ring having therein one to three heteroatoms independently selected from nitrogen, oxygen or sulfur. The nitrogen and sulfur heteroatoms can be optionally oxidized, and the nitrogen heteroatom can be optionally quaternized. Representative heterocycles of this type include pyrrolidinyl, piperidinyl, pyrazinyl, pyrazolyl, pyridazinyl morpholinyl, piperazinyl, thiomorpholinyl, pyridyl, pyrimidinyl, quinolyl, furyl, benzofuryl, thienyl, thiazolyl, pyrimidyl, indolyl, imidazolyl, isothiazolyl, isoxazolyl, oxadiazolyl, oxazolyl, 1,2,3-oxadiazolyl, thienyl, triazolyl 1,3,4-thiadiazolyl, and tetrazolyl, and the like.

The term "heterocycle," as used herein, also includes compounds of formula

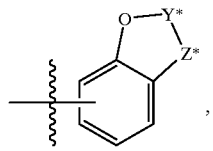

wherein Y* is selected from —C(O)— and —C(R$^{15}$)(R$^{15}$))$_v$—, wherein R$^{15}$ are independently hydrogen or alkyl, and v is 1, 2, or 3; and Z* is —CH$_2$—, —O—, —CH$_2$S(O)$_t$—, wherein t is zero, one, or two, —CH$_2$O—, —CH$_2$NR$^{20}$—, or —NR$^{20}$—, wherein R$^{20}$ is hydrogen or alkyl.

The term "heterocycle," as used herein, also includes bicyclic or tricyclic rings, wherein any of the aformentioned heterocycles are fused to one or two rings independently selected from an aryl ring, a cycloalkyl ring, a cycloalkenyl ring, or another monocyclic heteroaryl ring. Representative heterocycles of this type include benzo[b]furanyl, benzo[b]thienyl, benzimidazolyl, cinnolinyl, imidazo[4,5-c]

pyridinyl, quinazolinyl, thieno[2,3-c]pyridinyl, thieno[3,2-b]pyridinyl, thieno[2,3-b]pyridinyl,indolizinyl, imidazo[1,2-a]pyridine, and the like and can be attached to the parent molecular group through either the heretoaryl group or the aryl, cycloalkyl, or cycloalkenyl group to which they are fused. The heterocycle groups of this invention can be optionally substituted.

The term "(heterocycle)alkyl," as used herein, refers to an alkyl group to which is attached at least one heterocycle.

The term "hydrolyzing agent," as used herein, refers to reagents capable of removing ester groups from carboxylic acids such as those summarized in step (d). Examples of hydrolyzing agents include lithium hydroxide, sodium hydroxide, potassium hydroxide, sodium carbonate, potassium carbonate, hydrochloric acid, sulfuric acid, or hydrobromic acid.

The term "hydroxy," as used herein, refers to —OH.

The term "hydroxyalkyl," as used herein, refers to an alkyl group to which is attached at least one hydroxy group.

The term "hydroxyaryl," as used herein, refers to an aryl group to which is attached at least one hydroxy group.

The term "hydroxyarylalkyl," as used herein, refers to an alkyl group to which is attached at least one hydroxyaryl group.

The term "perchloroalkyl," as used herein, refers to an alkyl group in which all of the hydrogen atoms have been replaced with chloride atoms.

The term "perfluoroalkyl," as used herein, refers to an alkyl group in which all of the hydrogen atoms have been replaced with fluoride atoms.

The term "pharmaceutically acceptable salt," as used herein, refers to salts which are suitable for use in contact with the tissues of humans and lower animals without undue toxicity, irritation, or allergic response and are commensurate with a reasonable benefit/risk ratio. Pharmaceutically acceptable salts are well-known in the art. For example, S. M. Berge, et al. describe pharmaceutically acceptable salts in detail in J. Pharmaceutical Sciences, 1977, 66: 1 et seq. The salts may be prepared in situ during the final isolation and purification of the compounds of the invention or separately by reacting a free base function with a suitable acid. Representative acid addition salts include acetate, adipate, alginate, citrate, aspartate, benzoate, benzenesulfonate, sulfate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, para-toluenesulfonate and undecanoate. Also, basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl, and stearyl chlorides, bromides and iodides; and arylalkyl halides such as benzyl and phenethyl bromides. Examples of acids which may be employed to form pharmaceutically acceptable acid addition salts include such inorganic acids as hydrochloric acid, hydrobromic acid, sulfuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, and ethylamine. Other representative organic amines useful for the formation of base addition salts include ethylenediamine, ethanolamine, diethanolamine, piperidine, and piperazine.

The term "pharmaceutically acceptable prodrugs," as used herein refers to, those prodrugs of the compounds of the present invention which are suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "prodrug," as used herein, represents compounds which are rapidly transformed in vivo to parent compounds by hydrolysis in blood. A thorough discussion is provided in T. Higuchi and V. Stella, "Prodrugs as Novel Delivery Systems," Vol. 14 of the A.C.S. Symposium Series, and in Edward B. Roche, ed., "Bioreversible Carriers in Drug Design," American Pharmaceutical Association and Pergamon Press, 1987.

The term "reducing agent," as used herein, refers to reagents capable of converting carboxylic acids to alcohols in the presence of ester groups such as those summarized in step (c). Examples of reducing agents include borane•dimethylsulfide, borane•tetrahydrofuran, and a mixture of sodium borohydride and boron trifluoride•etherate.

The term "second base," as used herein, refers to compounds soluble in the second solvent system which are capable of selectively hydrolyzing ester groups in the presence of other ester groups such as those summarized in step (b). Examples of second bases include hydroxides such as lithium hydroxide, sodium hydroxide, and potassium hydroxide; and carbonates such as potassium carbonate and sodium carbonate.

The term "second halogenating agent," as used herein, refers to reagents or combinations of reagents useful for the conversion of carboxylic acid groups to carboxylic acid halides such as those summarized in step (f). Examples of second halogenating agents include thionyl chloride, a mixture of oxalyl chloride and N,N-dimethylformamide, and a mixture of thionyl chloride and N,N-dimethylformamide.

The term "second solvent system," as used herein, refers to a solvent mixture in which the selective hydrolysis described in step (b) is maximized due to the solubility of each reactant in the solvent mixture. The preferred second solvent system of the instant invention comprises water and an organic component, the organic component comprising tetrahydrofuran and methanol.

The term "sulfhydryl," as used herein, refers to —SH.

The term "sulfhydrylalkyl," as used herein, refers to an alkyl group to which is attached at least one sulfhydryl group.

The term "sulfone," as used herein, refers to —$SO_2$—.

The term "sulfonating agents," as used herein, refers to compounds which, when reacted with alcohols, form sulfonate leaving groups. Examples of sulfonating agents include trifluoromethanesulfonyl chloride and trifluoromethanesulfonic anhydride.

The term "sulfoxide," as used herein, refers to —SO—.

The term "thiocarbonyl," as used herein, refers to —C(=S)—

The term "thioalkoxy," as used herein, refers to an alkyl group attached to the parent molecular group through a sulfur atom. The thioalkoxy groups of this invention can be optionally substituted with one, two, or three halo substituents.

The term "thioalkoxyalkyl," as used herein, refers to an alkyl group to which is attached at least one thioalkoxy group.

The term "thiocycloalkoxy," as used herein, refers to a cycloalkyl group attached to the parent molecular group through a sulfur atom.

The term "thiocycloalkoxyalkyl," as used herein, refers to an alkyl group to which is attached at least one thiocycloalkoxy group.

The term "third base," as used herein, refers to a compounds capable of accepting protons which are useful for useful for promoting amide and amine formation reactions such as those summarized in step (g) and step (h), respectively. Examples of third bases include trialkylamines such as triethylamine and diisopropylamine; heterocyclic amines such as imidazole, pyridine, pyridazine, pyrimidine, and pyrazine; bicyclic amines such as DBN and DBU; carbonates such as sodium carbonate, potassium carbonate, sodium bicarbonate; and phosphates such as potassium phosphate and potassium hydrogen phosphate.

Synthetic Methods

Abbreviations

Abbreviations which have been used in the descriptions of the schemes and the examples that follow are: DBN for 1,5-diazobicyclo[4.3.0]non-5-ene; DBU for 1,8-diazobicyclo[5.4.0]undec-7-ene; dba for dibenzylidine acetone; DMA for N,N-dimethylacetamide; DMAP for 4-(N,N-dimethylamino)pyridine; DME for dimethoxyethane; DMF for N,N-dimethylformamide; DMSO for dimethylsulfoxide; MTBE for methyl tert-butyl ether; TEA for triethylamine; TFA for trifluoroacetic acid; THF for tetrahydrofuran.

The compounds and processes of the instant invention will be better understood in connection with the following synthetic schemes which illustrate the methods by which the compounds of the invention can be prepared. The compounds defined above can be prepared by a variety of synthetic routes. A representative procedure is shown in Scheme 1. The groups $R^1$, $R^4$, $R^5$, $R^6$, $R^7$, and $R^8$ are defined above. It will be readily apparent to one of ordinary skill in the art that the compounds defined above can be synthesized by substitution of the appropriate reactants and agents in the syntheses shown below. It will also be apparent to one skilled in the art that the selective protection and deprotection steps, as well as the order of the steps themselves, can be carried out in varying order, depending on the nature of $R^1$, $R^4$, $R^5$, $R^6$, $R^7$, and $R^8$, to successfully complete the syntheses of compounds of the instant invention. A thorough discussion of protecting groups is provided in Greene and Wuts, "Protective Groups in Organic Synthesis," 2nd ed., John Wiley & Son, Inc., 1991.

The precursor compounds are commercially available or can be prepared from commercially available starting materials. For example, compounds containing an alcohol group can be elaborated to alkyl, alkenyl, alkynyl, carboxaldehyde, ether, ester, amide, amine, thioalkoxide, sulfinyl, or sulfonyl by means well known in the art. Many of these groups can be further elaborated to other groups such as carbonates, carbamates, or ureas. Functional group transformations useful for preparing precursor compounds are disclosed in Larock, "Comprehensive Organic Transformations. A Guide to Functional Group Preparations," VCH Publishers, New York (1989).

The process of the instant invention can be interrupted at any time to isolate one or more intermediates formed during the process. These intermediates can be used for structure verification or preparation the solutions of known concentrations for HPLC analysis. In a preferred embodiment, the instant invention is is performed as a continuous process. The term "continuous process," as used herein, refers to the conduction of steps (a) through (h) being performed in a single pot without isolation of the intermediates.

Scheme 1

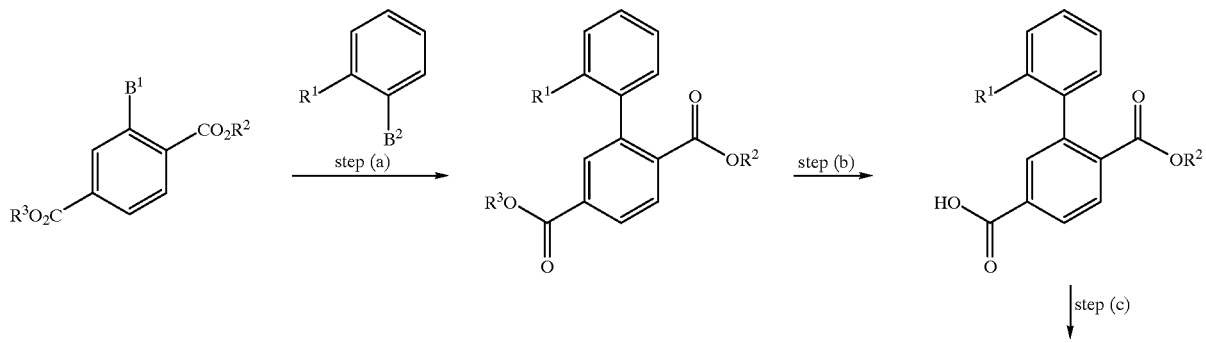

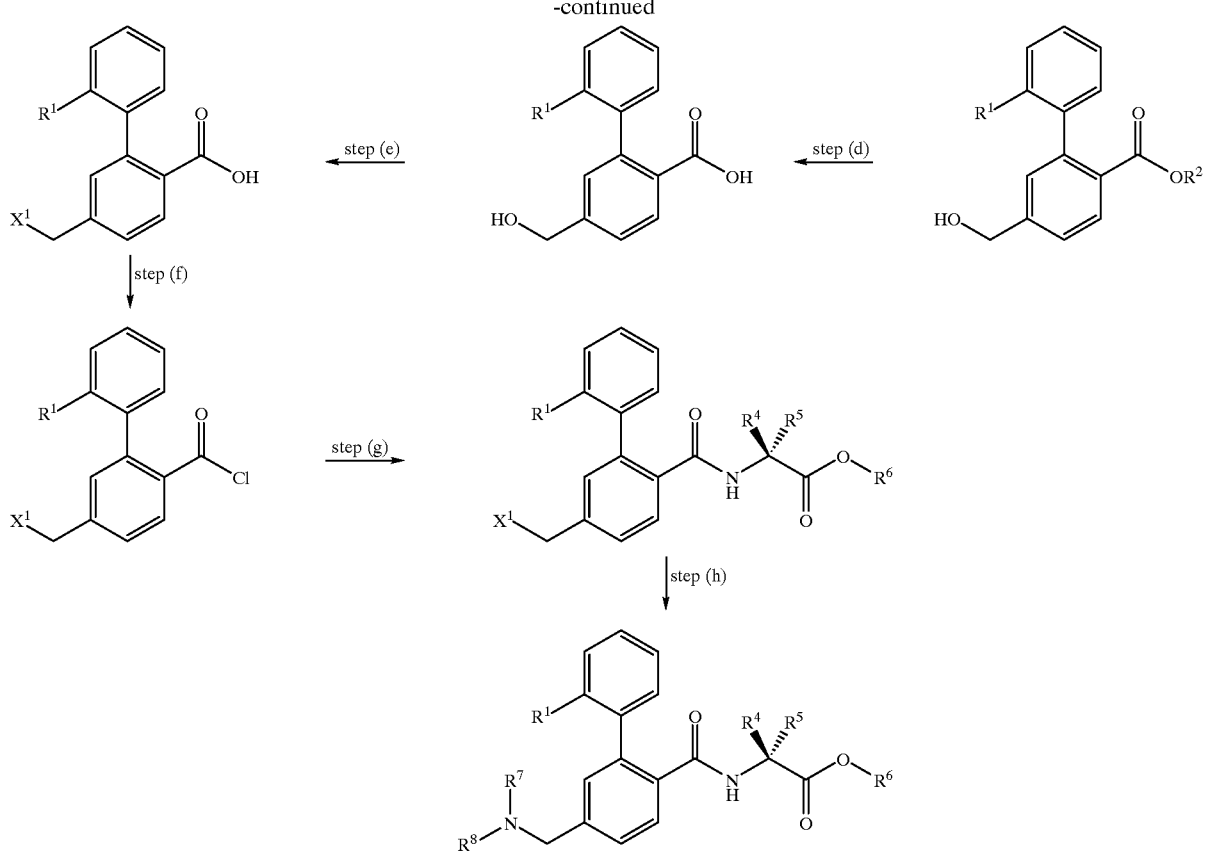

As shown in Scheme 1, preparation of first intermediate can be achieved by coupling of the two appropriately substituted phenyl rings in the presence of a catalyst such as tetrakis(triphenylphosphine)palladium(0), palladium(II) acetate, $Pd_2Cl_2(dba)$, or $PdCl_2 \cdot CH_2Cl_2$. Each of the aforementioned catalysts can be used with triphenylphosphine, triphenylarsine, or a trialkylphosphine such as tributylphosphine optionally present. The starting materials are either commercially available or can be prepared by means well known in the art. Although the solvent used in the reaction is not particularly limited, a solvent which is not reactive with the starting materials and in which the starting materials are at least partially soluble is generally used. Examples of such solvents include THF, dioxane, benzene, toluene, or mixtures thereof. Since acid is liberated with the progress of the reaction, it is preferable to run the reaction with at least a stoichiometric amount of base present. Preferred bases include potassium carbonate, potassium bicarbonate sodium carbonate, sodium bicarbonate, cesium fluoride, potassium phosphate, potassium dihydrogen phosphate, or potassium hydrogen phosphate. Although the reaction generally proceeds at elevated temperature, it can be run at lower temperatures, as needed. The reaction time is generally about 30 minutes to about 18 hours and can be selected depending on the types of starting materials and the reaction temperature. In a preferred embodiment, this conversion is achieved with dimethyl iodoterephthalate, ortho-tolylboronic acid, palladium(II) acetate, triphenylphosphine and sodium carbonate, each of which are commercially available, in toluene at about 75° C. for about 4 hours.

Conversion of the first intermediate to the second intermediate can be achieved by treatment of the former with base such as lithium hydroxide, sodium hydroxide, or potassium hydroxide. The solvent used for this reaction is typically one in which the starting material, base, and product are soluble and which promotes the desired selective hydrolysis. For this reason, mixtures of water and water-miscible solvents such as THF, dioxane, methanol, ethanol, propanol, iso-propanol can be used. The reaction is generally run below ambient temperature during addition of the base but can be warmed, as necessary. The reaction time is generally about 30 minutes to about 18 hours and can be selected depending on the types of starting materials and the reaction temperature. In a preferred embodiment, this conversion is achieved with lithium hydroxide in a mixture of water, THF, and methanol, wherein the methanol is present in at least one molar equivalent for every 2 molar equivalent of THF, at from about 0° C. to ambient temperature, for about 18 hours.

Conversion of the second intermediate to provide the third intermediate can be achieved by treatment of the former with a reducing agent such as borane•dimethylsulfide, borane•tetrahydrofuran, or a mixture of sodium borohydride or boron trifluoride•etherate. Although the solvent used in the reaction is not particularly limited, a solvent which is not reactive with the starting materials and in which the starting materials are at least partially soluble is generally used. Examples of such solvents include ethers such as THF, dioxane, diethyl ether, or mixtures thereof. The reaction is generally run at low temperatures but can be warmed, as necessary. The reaction time is generally about 30 minutes to about 18 hours and can be selected depending on the types of starting materials and the reaction temperature. In a preferred embodiment, this conversion is achieved with borane•dimethylsulfide in THF at from about 0° C. to ambient temperature for about 8 hours.

Conversion of the third intermediate to the fourth intermediate can be achieved by treatment of the former with a base such as lithium hydroxide, sodium hydroxide, potassium hydroxide, sodium carbonate, or potassium carbonate or an acid such as hydrochloric acid, sulfuric acid, or hydrobromic acid. Although the solvent used in the reaction is not particularly limited, a solvent which is not reactive with the starting materials and in which the starting materials are at least partially soluble is generally used. Examples of such solvents include water, benzene, toluene, THF, dioxane, benzene, toluene, acetonitrile, chloroform, dichloromethane, DMF, DMSO, alcohols such as methanol, ethanol, propanol, iso-propanol, and tert-butanol, or mixtures thereof. The reaction is generally run at elavated temperatures but can be lowered, as necessary. The reaction time is generally about 30 minutes to about 18 hours and can be selected depending on the types of starting materials and the reaction temperature. In a preferred embodiment, this conversion is achieved with sodium hydroxide in water and methanol at about 75° C. for about 1.5 hours.

Conversion of the fourth intermediate to the fifth intermediate can be achieved by treatment of the former with a halogenating agent such as hydrobromic acid phosphorus tribromide or a halogenating agent formed by mixing N-bromosuccinimide, carbon tetrabromide, tribromomethane, lithium bromide, phosphorus tribromide or lithium bromide with triphenylphosphine. Although the solvent used in the reaction is not particularly limited, a solvent which is not reactive with the starting materials and in which the starting materials are at least partially soluble is generally used. Examples of such solvents include water, acetic acid, benzene, toluene, THF, dioxane, chloroform, dichloromethane, DMF, DMSO, or mixtures thereof. The reaction is generally run at ambient temperature but can be raised or lowered, as necessary. The reaction time is generally about 30 minutes to about 18 hours and can be selected depending on the types of starting materials and the reaction temperature. In a preferred embodiment, this conversion is achieved with hydrobromic acid in toluene at about 75° C. for about 3 hours.

Conversion of the the fifth intermediate to the sixth intermediate can be achieved by treatment of the former with a halogenating agent such as thionyl chloride with or without DMF or oxalyl chloride with DMF. Although the solvent used in the reaction is not particularly limited, a solvent which is not reactive with the starting materials and in which the starting materials are at least partially soluble is generally used. Examples of such solvents include benzene, toluene, THF, dioxane, chloroform, dichloromethane, or mixtures thereof. The reaction is generally run at ambient temperature but can be raised or lowered, as necessary. The reaction time is generally about 30 minutes to about 18 hours and can be selected depending on the types of starting materials and the reaction temperature. In a preferred embodiment, this conversion is achieved with oxalyl chloride and DMF in toluene at ambient temperature for about 3.5 hours.

Conversion of the sixth intermediate to the seventh intermediate can be achieved by treatment of the former with an amino ester. The amino esters are commercially available or can be prepared from the appropriately substituted and protected amino acid by means well known in the art. Although the solvent used in the reaction is not particularly limited, a solvent which is not reactive with the starting materials and in which the starting materials are at least partially soluble is generally used. Examples of such solvents include benzene, toluene, THF, dioxane, chloroform, dichloromethane, or mixtures thereof. Since acid is liberated with the progress of a reaction, it is preferable to run the reaction in the presence of at least a stoichiometric amount of a deacidifying agent such as triethylamine, pyridine, diisopropylethylamine, sodium carbonate, potassium carbonate, sodium bicarbonate, potassium phosphate, or potassium hydrogen phosphate. Although the reaction generally proceeds at room temperature, it can be run at lower temperatures, as needed. The reaction time is generally 15 minutes to 2 hours and can be arbitrarily selected depending on the types of starting materials and reaction temperature. In a preferred embodiment, this conversion is achieved with L-methionine, methyl ester and triethylamine in toluene below about 10° C. for about 15 minutes.

Conversion of the seventh intermediate to compounds of formula (I) can be achieved by treatment of the former with an amine in the presence of base. Although the solvent used in the reaction is not particularly limited, a solvent which is not reactive with the starting materials and in which the starting materials are at least partially soluble is generally used. Examples of such solvents include benzene, toluene, THF, dioxane, chloroform, dichloromethane, acetonitrile, DMF, DMSO, or mixtures thereof. Since acid is liberated with the progress of a reaction, it is preferable to run the reaction in the presence of at least a stoichiometric amount of a deacidifying agent such as triethylamine, pyridine, diisopropylethylamine, sodium carbonate, potassium carbonate, sodium bicarbonate, potassium phosphate, or potassium hydrogen phosphate. Although the reaction generally proceeds at room temperature, it can be run at lower temperatures, as needed. The reaction time is generally about 30 minutes to about 18 hours and can be arbitrarily selected depending on the types of starting materials and reaction temperature. In a preferred embodiment, this conversion is achieved with N-butyl-N-cyclohexylethylamine and potassium carbonate in a mixture of toluene and acetonitrile below ambient temperature for about 18 hours.

The compounds and processes of the present invention will be better understood in connection with the following examples, which are intended as an illustration of and not a limitation upon the scope of the invention.

EXAMPLE 1A

Dimethyl 2'-methyl(1,1'-biphenyl)-2.5-dicarboxylate

A mixture of dimethyl iodoterephthalate (2.41 kg, 7.53 mol), ortho-tolylboronic acid (1.23 kg, 9.04 mol), palladium (II) acetate (16.9 g, 0.08 mol), and triphenylphosphine (79.0 g, 0.30 mol) in deoxygenated toluene (19 L) and 2M $Na_2CO_3$ (19 L) was vigorously mechanically stirred for 4 hours at 75–80° C. and cooled to room temperature to provide two distinct layers. The layers were separated, and the organic layer was filtered through a pad of silica gel 60 (4.79 kg of silica gel slurried with 2×10 L of MTBE) with a 40 L MTBE rinse, concentrated to 40 L, stored at 2–8° C. for 18 hours, filtered through a pad of diatomaceous earth (4.91 kg of Celite® 521 slurried in 20 L of MTBE) with a 40 L MTBE rinse to provide a solution of 2.12 kg (99%) of the desired product in MTBE.

MS (DCI/$NH_3$) m/z 302 (M+$NH_4$);

$^1H$ (CDCl$_3$) δ 8.10–7.93 (m, 3H), 7.32–7.21 (m, 3H), 7.07 (br d, J=7.7 Hz, 1H), 3.93 (s, 3H), 3.63 (s, 3H), 2.07 (s, 3H);

$^{13}C$ (CDCl$_3$) δ 167.2 (q), 166.2 (q), 142.8 (q), 140.3 (q), 135.2 (q), 134.4 (q), 132.6 (q), 132.0 (CH), 129.9 (CH), 129.6 (CH), 128.4 (CH), 128.1 (CH), 127.6 (CH), 125.3 (CH), 52.4 ($CH_3$), 52.1 ($CH_3$), 20.0 ($CH_3$);
retention time: 14.8 minutes (4.6 mm×25 cm Zorbax SB-C8 column with a mobile phase comprising 1:1 water with 0.1% $H_3PO_4$/acetonitrile, a flow rate of 1.5 mL/min for 30 minutes at ambient temperature, and UV detection at 210 nm).

EXAMPLE 1B 6-(methoxycarbonyl)-2'-methyl(1,1'-biphenyl)-3-carboxylic Acid

A solution of Example 1A (4.16 kg, 8.48 mol) in MTBE (65 L) was concentrated to about 16 L, treated with methanol (16 L), concentrated to about 16 L, treated sequentially with THF (33 L) and methanol (9.5 L), cooled to less than 10° C. (ice/water), treated with 2M LiOH solution (8.8 L) such that the temperature was below 10° C., stirred at ambient temperature for 18 hours, concentrated below 25° C. to about one third of its original volume, poured into water (5 L), washed with hexanes (6 L), treated sequentially with MTBE (30 L) and 3M HCl until pH 6.01, filtered through diatomaceous earth (1 kg of Celite® 521 slurried with 4.6 L of MTBE) with a 30 L MTBE rinse, and concentrated to 35 L to provide a solution of the desired product in MTBE.

MS (DCI/$NH_3$) m/z 269 (M−H)⁻;

$^1$H (300 MHz, $CDCl_3$) δ 8.17–8.14 (m, 1H), 8.03 (d, J=2.9 Hz, 1H), 8.01 (d, J=2.6 Hz, 1H), 7.30–7.19 (m, 3H), 7.09 (br dd, J=7.4 Hz, 0.8 Hz, 1H), 3.64 (s, 3H), 2.08 (s, 3H);

$^{13}$C (300 MHz, $CDCl_3$) δ 171.3 (q), 167.2 (q), 142.9 (q), 140.0 (q), 135.4 (q), 135.3 (q), 132.6 (CH), 131.7 (q), 130.0 (CH), 129.7 (CH), 128.7 (CH), 128.5 (CH), 127.8 (CH), 125.4 (CH), 52.2 ($CH_3$), 20.0 ($CH_3$);
retention time: 5.2 minutes (4.6 mm×25 cm Zorbax SB-C8 column with a mobile phase comprising 1:1 water with 0.1% $H_3PO_4$/acetonitrile, a flow rate of 1.5 mL/min for 30 minutes at ambient temperature, and UV detection at 210 nm).

EXAMPLE 1C

Methyl 5-(hydroxymethyl)-2'-methyl(1,1'-biphenyl)-2-carboxylate

A solution of Example 1B (12.96 kg of a 10.4 wt % solution, 1.35 kg, 4.99 mol) in MTBE over 3 Å molecular sieves was decanted, cooled to 5° C. (ice/methanol), treated with Borane•dimethyl sulfide (0.9 L, 9 mol) with mechanical stirring such that the internal temperature was below 10° C., warmed to room temperature for 8 hours, cooled to 5° C., treated with methanol (1 L) with stirring such that the internal temperature remained below 10° C., stirred for 10 minutes, warmed to room temperature, and washed with 1M sodium hydroxide (10 kg). The layers were separated, and the organic layer was treated with 1M sodium hydroxide (10 kg), stirred for 30 minutes, and filtered through diatomaceous earth (200 g of Celite® 545) with a 500 g MTBE rinse. The filtrate was concentrated, and the residue was treated with methanol (9.5 kg) and concentrated to provide 2.49 kg (69% for 2 steps) of the desired product as a thick oil.

MS (DCI/$NH_3$) m/z 274 (M+$NH_4$)⁺;

1H (300 MHz, $CDCl_3$) δ 7.83 (d, J=7.7 Hz, 1H), 7.28 (br dd, J=7.3 Hz, 1.5 Hz, 1H), 7.12–7.05 (m, 4H), 6.92 (br dd, J=6.9 Hz, 1.1 Hz, 1H), 4.64 (s, 2H), 3.47 (s, 3H), 1.92 (s, 3H);

$^{13}$C (300 MHz, $CDCl_3$) δ 167.6 (q), 144.7 (q), 143.2 (q), 141.3 (q), 135.2 (q), 130.3 (CH), 129.3 (CH), 129.2 (q), 128.9 (CH), 128.4 (CH), 128.3 (CH), 127.2 (CH), 125.2 (CH), 64.4 ($CH_2$), 51.8 ($CH_3$), 19.9 ($CH_3$).
retention time: 10.1 minutes(4.6 mm×25 cm Zorbax SB-C8 column with a mobile phase comprising 7:3 water with 0.1% $H_3PO_4$/acetonitrile, a flow rate of 1.5 mL/min for 25 minutes at ambient temperature, and UV detection at 210 nm).

EXAMPLE 1D 5-(hydroxymethyl)-2'-methyl(1,1'-biphenyl)-2-carboxylic Acid

A solution of Example 1C in methanol (8.04 kg of 30.4 wt % solution, 2.44 kg, 9.52 mol) was diluted with methanol (12 L), cooled to 3° C. (ice/water), treated with 2M sodium hydroxide (10.6 L) such that the temperature remained less than 30° C., heated to 75° C. for 1.5 hours, cooled to ambient temperature, concentrated to about one third of its original volume, washed with iso-propyl acetate (2.5 L), and treated sequentially with ethyl acetate (19.2 L) and 3M HCl to pH 2. The resulting two layers were separated, and the organic layer was washed with water (9.5 L), concentrated to about one half its original volume, treated with toluene (11 L), concentrated to about one half of its original volume, treated with toluene, (13 L), and cooled to 5° C. (ice/methanol) to precipitate a solid. The mixture was filtered, and the solid was washed with 9:1 toluene/ethyl acetate (600 mL), loaded onto trays, and dried under vacuum with a nitrogen bleed at ambient temperature for 48 hours to provide 2.02 kg (87%) of the desired product.

MS (DCI/$NH_3$) m/z 260 (M+$NH_4$)⁺ and 502 (2M+$NH_4$)⁺;

$^1$H (300 MHz, $CD_3OD$) δ 7.83 (d, J=7.8 Hz, 1H), 7.33 (d, J=7.8 Hz, 1H), 7.14–7.03 (m, 4H), 6.93 (d, J=7.1 Hz, 1H), 4.76 (br s, 2H), 4.58 (s, 2H), 1.96 (s, 3H);

$^{13}$C (300 MHz, $CD_3OD$) δ 171.1 (q), 147.0 (q), 144.6 (q), 143.4 (q), 136.7 (q), 131.5 (CH), 131.3 (q), 130.6 (CH), 130.4 (CH), 129.8 (CH), 128.3 (CH), 126.5 (CH), 126.4 (CH), 64.5 ($CH_2$), 20.2 ($CH_3$).
retention time: 10.9 minutes(4.6 mm×25 cm Zorbax SB-C8 column with a mobile phase comprising 9:1 water with 0.1% $H_3PO_4$/acetonitrile, a flow rate of 1.5 mL/min for 25 minutes at 35° C., and UV detection at 210 nm).

EXAMPLE 1E 5-(bromomethyl)-2'-methyl(1,1'-biphenyl)-2-carboxylic Acid

A solution of Example 1D (1.98 kg, 8.17 mol) in toluene (16 L) at room temperature was treated with aqueous HBr (13.8 L, 123 mol), degassed by vigorous nitrogen bubbling for 30 minutes, heated at 75° C. for 3 hours, cooled to room temperature, and added to toluene (16 L) to provide two layers. The layers were separated, and the organic layer was washed with water (2×8.4 L) and concentrated to about 15 L to provide a solution of the desired product in toluene.

MS (DCI/$NH_3$) m/z 322 (M+$NH_4$)⁺;

$^1$H ($CDCl_3$) δ 7.91 (d, J=8.1 Hz, 1H), 7.35 (dd, J=8.1 Hz, 2.0 Hz, 1H), 7.19–7.09 (m, 4H), 6.98 (dd, J=7.4 Hz, 1.2 Hz, 1H) 4.39 (s, 2H), 1.97 (s, 3H);

$^{13}$C ($CDCl_3$) δ 172.2 (q), 144.3 (q), 142.3 (q), 140.6 (q), 135.3 (q), 132.0 (CH), 131.6 (CH), 129.7 (CH), 129.0 (q), 128.5 (CH), 127.8 (CH), 127.6 (CH), 125.4 (CH), 31.7 ($CH_2$), 19.8 ($CH_3$);
retention time: 12.1 minutes (4.6 mm×25 cm Zorbax SB-C8 column with a mobile phase comprising 9:1 water with 0.1% $H_3PO_4$/acetonitrile, a flow rate of 1.5 mL/min for 5 minutes at 35° C., and UV detection at 210 nm).

21

EXAMPLE 1F (1S)-1-(methoxycarbonyl)-3-(methylsulfanyl)propyl 5-(bromomethyl)-2'-methyl(11'-biphenyl)-2-carboxylate A solution of Example 1E and DMF (3 mL) in toluene (6.73 kg of a 17.8 wt % solution, 3.93 mol) was diluted with toluene (2.9 L), treated with oxalyl chloride (411 mL) over 15 minutes, stirred for 3.5 hours, concentrated to about one half of its original volume, diluted with toluene (3.4 L), cooled to 5° C., (ice/water), treated with L-methionine, methyl ester hydrochloride (1.18 kg, 5.90 mol) and with triethylamine over 1 hour such that the internal temperature remained below 10° C., stirred for 15 minutes, treated with 1M $H_3PO_4$ (4.6 L), and stirred for 5 minutes to provide two layers. The organic layer was separated and washed with 1M $H_3PO_4$ (4.6 L) to provide a solution of the desired product in toluene.

EXAMPLE 1G (1S)-1-(methoxycarbonyl)-3-(methylsulfanyl)propyl 5-((butyl(2-cyclohexylethyl)amino)methyl)-2'-methyl(1,1'-biphenyl)-2-carboxylate A mixture of N-butyl-N-cyclohexylethylamine hydrochloride (1.2 kg, 5.5 mol), the solution of Example IF in toluene, and acetonitrile (5.9 L) was treated with 2M aqueous $K_2CO_3$ (4.6 L), vigorously degassed with nitrogen, stirred for 18 hours, concentrated to remove the acetonitrile, washed sequentially with 1M acetic acid (2×4.6 L), 2M $K_2CO_3$ (4.6 L) and water (4.7 L), and concentrated to about one third of its original volume to provide a solution of 2.03 kg (94%) of the desired product in toluene.

MS (DCI/$NH_3$) m/z 553 (M+H)$^+$;

$^1$H (CDCl$_3$) δ 7.90 (dd, J=15.1 Hz, 8.1 Hz, H), 7.41 (dd, J=8.0 Hz, 1.4 Hz, 1H), 7.35–7.14 (m, 5H), 5.89 (d, J=7.4 Hz, 1H), 4.65–4.60 (m, 1H), 3.66 (s, 3H), 3.58 (s, 2H), 2.44 (d, J=7.0 Hz, 2H), 2.39 (d, J=7.0 Hz, 2H), 2.18 (s, 1H), 2.08–2.00 (m, 8H), 1.89–1.82 (m, 1H), 1.70–1.12 (m, 17H), 0.87 (t, J=7.4 Hz, 3H);

retention time: 8.6 minutes (4.6 mm×25 cm Chiralpak AD column with a mobile phase comprising 9:1 hexane/ethanol, a flow rate of 0.7 mL/min for 30 minutes at ambient temperature, and UV detection at 210 nm).

EXAMPLE 1H (2S)-2-(((5-((butyl(2-cyclohexylethyl)amino)methyl)-2'-methyl(1,1'-biphenyl)-2-yl)carbonyl)amino)-4-(methylsulfanyl)butanoic Acid A solution of Example 1F in toluene was treated with methanol (7.5 L), concentrated to about one third of its original volume, treated with methanol (7.5 L), concentrated to about one quarter of its original volume, treated with methanol (2.5 L) and THF (7.5 L), cooled to –10° C., (methanol/dry ice), treated with 1M LiOH (9 L) such that the internal temperature remained below –5° C., stirred at –10° C. for 15 minutes and at room temperature for 18 hours, concentrated to about one third of its original volume, treated with isopropyl acetate (7.6 L) with stirring, and adjusted to pH 5.0 with 1M $H_3PO_4$ to provide two layers. The layers were separated, and the organic layer was washed with water (3.7 L), concentrated to about one half of its original volume, treated with iso-propyl acetate (4.3 L), and concentrated to about one half its original volume to provide a solution of 2.37 kg (97%) of the desired product in iso-propyl acetate.

22

$^1$H (DMSO-d$_6$) δ 9.12 (br s, 1H), 7.63 (d, J=7.9 Hz, 1H), 7.56–7.49 (m, 2H), 7.29 (s, 1H), 7.16–7.01 (m, 4H), 4.29 (s, 2H), 4.18 (dt, J=4.4 Hz, 8.4 Hz, 1H), 2.99 (d, J=8.8 Hz, 2H), 2.95 (d, J=8.6 Hz, 2H), 2.16–2.0 (m, 2H), 1.98 (s, 3H), 1.86 (s, 3H), 1.80–1.45 (m, 11H), 1.25–1.00 (m, 7H), 0.87–0.80 (m, 1H), 0.78 (t, J=7.6 Hz, 3H);

$^{13}$C (DMSO-d$_6$) δ 172.3 (q), 167.4 (q), 139.4 (q), 139.2 (q), 137.2 (q), 135.1 (q), 132.6 (CH), 131.0 (q), 129.4 (CH), 129.3 (CH), 129.0 (CH), 128.0 (CH), 127.4 (CH), 124.9 (CH), 55.6 (CH$_2$), 52.0 (CH$_2$), 51.0 (CH), 50.5 (CH$_2$), 34.6 (CH), 31.8 (CH$_2$), 30.4 (CH$_2$), 29.5 (CH$_2$), 29.2 (CH$_2$), 25.3 (CH$_2$), 24.9 (CH$_2$), 24.5 (CH$_2$), 19.2 (CH$_3$), 18.8 (CH$_2$), 14.0 (CH$_3$), 12.6 (CH$_3$);

retention time: 6.2 minutes (4.6 mm×25 cm Chirobiotic T column with a mobile phase comprising 7:3 10 mM $KH_2PO_4$ (pH 6.5)/$CH_3CN$, a flow rate of 1 mL/min for 10 minutes, a column temperature of 35° C., and UV detection at 205 nm).

EXAMPLE 1I (2S)-2-(((5-((butyl(2-cyclohexylethyl)amino)methyl)-2'-methyl(11'-biphenyl)-2-yl)carbonyl)amino)-4-(methylsulfanyl)butanoic Acid, Sulfuric Acid Salt The solution of Example 1H was solvent exchanged from iso-propyl acetate to MEK by twice concentrating the solution to an oil under reduced pressure and dissolving the oil in peroxide-free MEK. The MEK solution was treated with 5M $H_2SO_4$ (1.05 eq) at room temperature, stirred until a precipitate formed, and azeotropically dried by repeated addition and distillation of MEK until the amount of water present in solution was below 2 mg/mL to provide a solid containing 99.3% of the desired product.

What is claimed is:

1. A process for preparing a compound of structural formula (I)

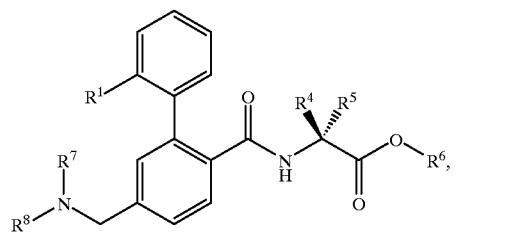

(I)

or a pharmaceutically acceptable salt or prodrug thereof, wherein $R^1$ is methyl, ethyl, propyl, iso-propyl, halo, or haloalkyl;

one of $R^4$ or $R^5$ is hydrogen or alkyl, and the other is alkenyl, alkoxyalkyl, alkoxyarylalkyl, alkoxycarbonylalkyl, alkylsulfinylalkyl, alkylsulfonylalkyl, alkyl, alkynyl, aminoalkyl, aminocarbonylalkyl, aminothiocarbonylalkyl, aryl, arylalkyl, carboxyalkyl, cyanoalkyl, cycloalkylalkoxyalkyl, cycloalkyl, cycloalkylalkyl, cycloalkylsulfinylalkyl, cycloalkylsulfonylalkyl, (heterocycle)alkyl, hydroxyalkyl, hydroxyarylalkyl, sulfhydrylalkyl, thioalkoxyalkyl optionally substituted with one, two, or three halo substituents, or thiocycloalkoxyalkyl;

$R^6$ is hydrogen or a carboxy protecting group; and $R^7$ and $R^8$ are independently hydrogen, alkenyl, alkyl, alkynyl, aryl, arylalkyl, cycloalkyl, cycloalkylalkyl, heterocycle, or (heterocycle)alkyl, wherein, at each occurence, the aryl and the heterocycle can be optionally substituted with one, two, three, four, or five substituents independently selected from alkenyl, alkyl, alkynyl, aryl, arylalkyl, cycloalkyl, cycloalkylalkyl, heterocycle, (heterocycle)alkyl, carboxaldehyde, azido, nitro, amino, cyano, hydroxy, sulfhydryl, and —$L^1$—$R^6$, wherein $L^1$ is —C(X)—, —S(O)$_t$—, —NR$^{12}$—, —O—, —X'C(X)—, —C(X)X'—, —N(R$^{12}$)C(O)N(R$^{12}$)—, —N(R$^{12}$)C(X)—, —C(X)N(R$^{12}$)—, —NR$^{12}$S(O)$_t$—, or —S(O)$_t$NR$^{12}$—; and wherein $R^6$ and $R^{12}$ are independently hydrogen, alkenyl, alkyl, alkynyl, aryl, arylalkyl, cycloalkyl, cycloalkylalkyl, heterocycle, or (heterocycle)alkyl; and wherein X and X' are independently O or S, and wherein t is zero, one, or two, the process comprising, (a) reacting a compound of structural formula

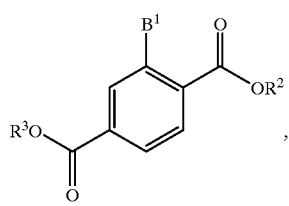

wherein $B^1$ is diazonium tetrafluoroborate, chloride, bromide, iodide, methylsulfonate, or trifluoromethylsulfonate; and $R^2$ and $R^3$ are independently alkyl, arylalkyl, cycloalkyl, or haloalkyl with a compound of structural formula

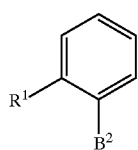

wherein $R^1$ is defined above, and B is —Sn(alkyl)$_3$, or —B(OR$^9$)(OR$^{10}$), wherein $R^9$ and $R^{10}$ are hydrogen or alkyl, or $R^{10}$ and $R^{11}$, together with the oxygen atoms to which they are attached, are alkylene, wherein the alkylene can be optionally substituted with one, two, three, or four alkyl substituents, in the presence of a catalyst and a first base, to provide a first intermediate of structural formula

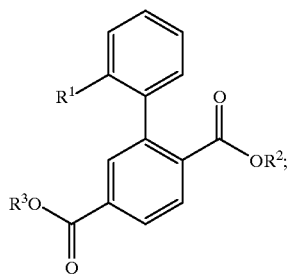

(b) reacting the first intermediate with a second base in a second solvent system, the second solvent system comprising water and an organic component, to provide a second intermediate of structural formula

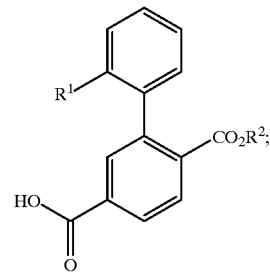

(c) reacting the second intermediate with a reducing agent to provide a third intermediate of structural formula

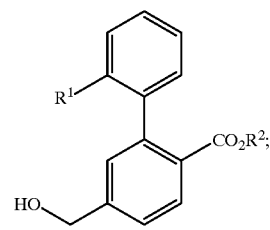

(d) reacting the third intermediate with a hydrolyzing agent to provide a fourth intermediate of structural formula

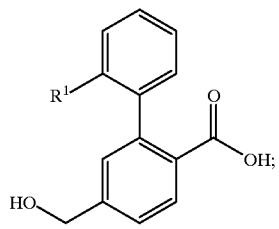

(e) reacting the fourth intermediate compound with first halogenating agent to provide a fifth intermediate of structural formula

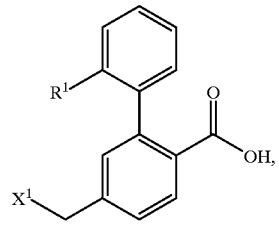

wherein $X^1$ is halo;

(f) reacting the fifth intermediate compound with a second halogenating agent to provide a sixth intermediate of structural formula

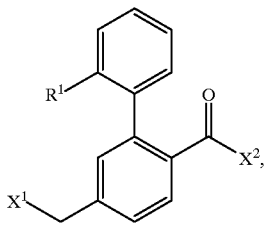

wherein $X^2$ is halo;

(g) reacting the sixth intermediate with a compound of structural formula

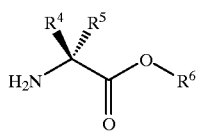

in the presence of a third base to provide a seventh intermediate of structural formula

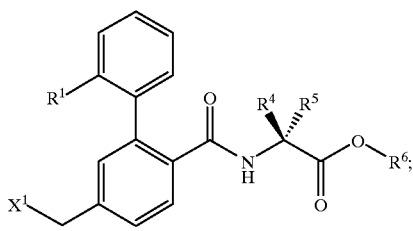

(h) reacting the seventh intermediate with $HN(R^7)(R^8)$ in the presence of the third base to provide the compound of structural formula (I), wherein $R^6$ is a carboxy-protecting group; and (i) reacting the compound of formula (I) with the second base to provide the compound of structural formula (I), wherein $R^6$ is hydrogen.

2. The process according to claim 1, wherein the compound of structural formula (I) is (2S)-2-(((5-((butyl(2-cyclohexylethyl)amino)methyl)-2'-methyl(1,1'-biphenyl)-2-yl)carbonyl)amino)-4-(methylsulfanyl)butanoic acid, or a pharmaceutically acceptable salt or prodrug thereof.

3. The process according to claim 1, wherein steps (a), (d), and (e) are performed at about 25° C. to about 100° C. for from about 1 hour to about 5 hours.

4. The process according to claim 1, wherein steps (b), (c), (h), and (i) are performed at about -10° C. to about 35° C. for from about 30 minutes to about 24 hours.

5. The process according to claim 1, wherein step (f) is performed at about -10° C. to about 35° C. for from about 30 minutes to about 4 hours.

6. The process according to claim 1, wherein step (g) is performed at about -10° C. to about 10° C. for from about 5 minutes to about 12 hours.

7. The process according to claim 1, wherein the catalyst is tetrakis(triphenylphosphine)palladium(0), palladium(II) acetate, $Pd_2Cl_2(dba)$, or $PdCl_2 \cdot CH_2Cl_2$ with triphenylphosphine, triphenylarsine or a trialkylphosphine optionally present; and the first base is potassium carbonate, potassium bicarbonate sodium carbonate, sodium bicarbonate, cesium fluoride, potassium phosphate, potassium dihydrogen phosphate, or potassium hydrogen phosphate.

8. The process according to claim 1, wherein the second base is lithium hydroxide, sodium hydroxide, potassium hydroxide, potassium carbonate, or sodium carbonate; and the organic component is a mixture of a first organic solvent and a second organic solvent, wherein the second organic is present in at least about one quarter part to about two parts per two parts of the first organic solvent.

9. The process according to claim 1, wherein the reducing agent is borane•dimethylsulfide, borane•tetrahydrofuran, or a mixture of sodium borohydride and boron trifluoride•etherate.

10. The process according to claim 1, wherein the hydrolyzing agent is lithium hydroxide, sodium hydroxide, potassium hydroxide, sodium carbonate, potassium carbonate, hydrochloric acid, sulfuric acid, or hydrobromic acid.

11. The process according to claim 1, wherein the organic component is a mixture of methanol and tetrahydrofuran.

12. The process according to claim 1, wherein the first halogenating agent is a mixture of N-bromosuccinimide and triphenylphosphine, a mixture of carbon tetrabromide and triphenylphosphine, a mixture of tribromomethane and triphenylphosphine, a mixture of lithium bromide and triphenylphosphine, phosphorus tribromide, a mixture of phosphorus tribromide and lithium bromide, or hydrobromic acid.

13. The process according to claim 1, wherein the second halogenating agent is thionyl chloride, a mixture of oxalyl chloride and N,N-dimethylformamide, or a mixture of thionyl chloride and N,N-dimethylformamide.

14. The process according to claim 1, wherein the third base is triethylamine, pyridine, diisopropylethylamine, sodium carbonate, potassium carbonate, sodium bicarbonate, potassium phosphate, or potassium hydrogen phosphate.

15. The process according to claim 1 which is performed as a continuous process.

16. A process for preparing (2S)-2-(((5-((butyl(2-cyclohexylethyl)amino)methyl)-2'-methyl(1,1'-biphenyl)-2-yl)carbonyl)amino)-4-(methylsulfanyl)butanoic acid, or a pharmaceutically acceptable salt or prodrug thereof, comprising (a) reacting a compound of structural formula

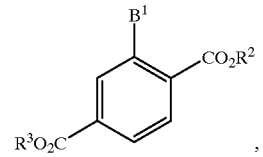

wherein $B^1$ is bromide, or iodide, and $R^2$ and $R^3$ are alkyl, with a compound of structural formula

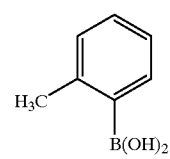

in the presence of tetrakis(triphenylphosphine)palladium(0), palladium(II) acetate and triphenylphosphine, $Pd_2Cl_2(dba)$ and triphenylphosphine, or $PdCl_2 \cdot CH_2Cl_2$ and triphenylphosphine with potassium carbonate, potassium bicarbonate sodium carbonate, sodium bicarbonate, or cesium fluoride at about 60° C. to 80° C. for about 2 hours to about 4 hours to provide a first intermediate of structural formula

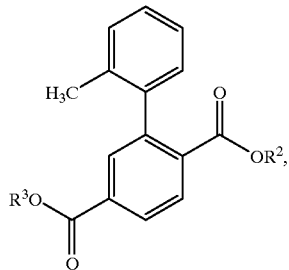

wherein $R^2$ and $R^3$ are defined above;

(b) reacting the first intermediate with lithium hydroxide at about −5° C. to about 10° C. for about 1 hour to about 18 hours in a second solvent system, the second solvent system comprising water and an organic component, the organic component comprising tetrahydrofuran and methanol, to provide a second intermediate of structural formula

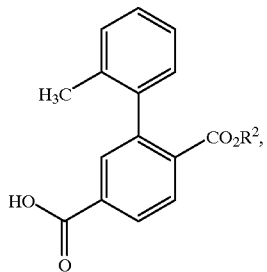

wherein $R^2$ is defined above;

(c) reacting the second intermediate with borane•dimethylsulfide or borane•tetrahydrofuran at about 0° C. to about 25° C. for about 18 hours to provide a third intermediate of structural formula

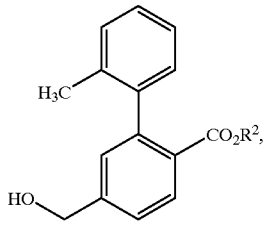

wherein $R^1$ and $R^2$ are defined above;

(d) reacting the third intermediate compound with lithium hydroxide, sodium hydroxide, or potassium hydroxide at about 60° C. to about 75° C. for about 1 hour to about 3 hours to provide a fourth intermediate of structural formula

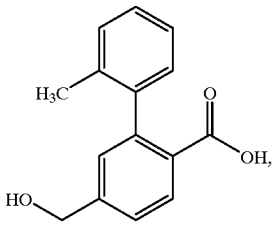

wherein $R^1$ is defined above;

(e) reacting the fourth intermediate with hydrobromic acid at about 60° C. to about 75° C. for about 30 minutes to about 4 hours to provide a fifth intermediate of structural formula

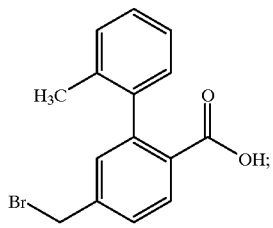

(f) reacting the fifth intermediate with oxalyl chloride and N,N-dimethylformamide at about 0° C. to about 35° C. for about 30 minutes to about 4 hours to provide a sixth intermediate of structural formula

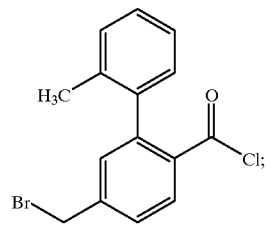

(g) reacting the sixth intermediate with a compound of structural formula

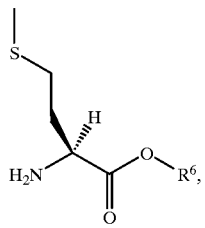

wherein and $R^6$ is a carboxy-protecting group, in the presence of triethylamine, pyridine, diisopropylethylamine, sodium carbonate, potassium carbonate, or sodium bicarbonate, at about −5° C. to about 10° C., for about 5 minutes to about 1 hour, to provide a seventh intermediate of structural formula

29

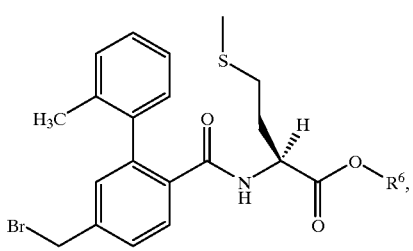

wherein R⁶ is a carboxy-protecting group;

(h) reacting the seventh intermediate with N-(2-cyclohexylethylethyl)-1-butanamine in the presence of triethylamine, pyridine, diisopropylethylamine, sodium carbonate, potassium carbonate, or sodium bicarbonate, at about −5° C. to about 25° C., for about 30 minutes to about 12 hours, to provide the compound of structural formula (II), wherein R⁶ a carboxy-protecting group; and (i) reacting the compound of formula (II), wherein R⁶ a carboxy-protecting group, with lithium hydroxide at a temperature of about −5° C. to about 25° C. to provide the (2S)-2-(((5-((butyl(2-cyclohexylethyl)amino)methyl)-2'-methyl(1,1'-biphenyl)-2-yl)carbonyl)-amino)4-(methylsulfanyl)butanoic acid.

17. A process for preparing a compound of structural formula (II)

(II)

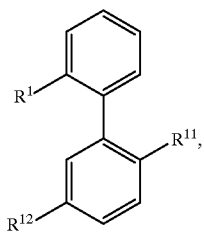

wherein

R¹ is methyl, ethyl, propyl, iso-propyl, halo, or haloalkyl;

R¹¹ is carboxy, halocarbonyl, or alkoxycarbonyl, wherein the alkoxycarbonyl can be optionally substituted with cycloalkyl, aryl, or halo; and R¹² is alkoxycarbonyl, wherein the alkoxycarbonyl can be optionally substituted with cycloalkyl, aryl, or halo, carboxy, hydroxymethyl, halomethyl, or —CH₂OSO₂R⁴, wherein R⁴ is alkyl, haloalkyl, or phenyl, wherein the phenyl can be optionally substituted with one, two, or three substituents independently selected from halo, nitro, alkyl, or haloalkyl, the process comprising:

30

(a) reacting a compound of structural formula

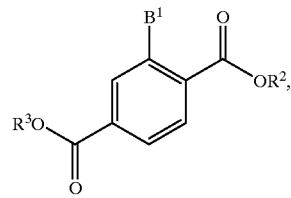

wherein B¹ is diazonium tetrafluoroborate, chloride, bromide, iodide, methylsulfonate, or trifluoromethylsulfonate; and R² and R³ are independently alkyl, arylalkyl, cycloalkyl, or haloalkyl with a compound of structural formula

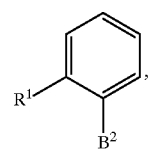

wherein R¹ is defined above, and B² is —Sn(alkyl)₃, or —B(OR⁹)(OR¹⁰), wherein R⁹ and R¹⁰ are hydrogen or alkyl, or R¹⁰ and R¹¹, together with the oxygen atoms to which they are attached, are alkylene, wherein the alkylene can be optionally substituted with one, two, three, or four alkyl substituents, in the presence of a catalyst and a first base, to provide a first intermediate of structural formula

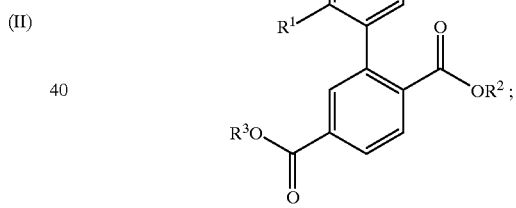

(b) optionally reacting the first intermediate with a second base in a second solvent system, the second solvent system comprising water and an organic component, to provide a second intermediate of structural formula

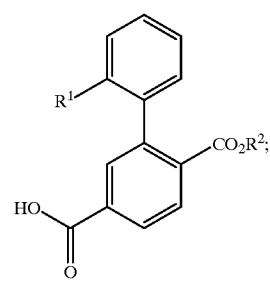

(c) optionally reacting the second intermediate with a reducing agent to provide a third intermediate of structural formula

31

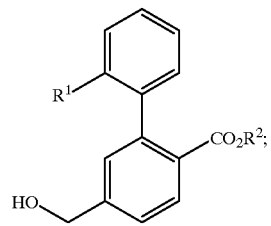

(d) optionally reacting the third intermediate with a hydrolyzing agent to provide a fourth intermediate of structural formula

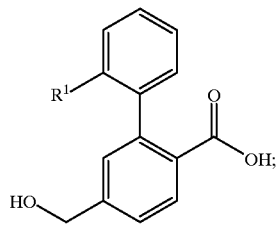

(e) optionally reacting the fourth intermediate compound with an activating agent optionally in the presence of a third base to provide a fifth intermediate of structural formula

32

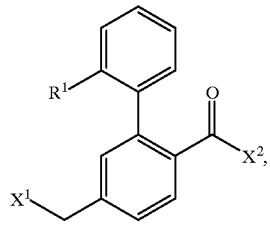

wherein $X^3$ is halo or $-OSO_2R^4$;

(f) optionally reacting the fifth intermediate compound with a second halogenating agent to provide a sixth intermediate of structural formula wherein $X^2$ is halo.

\* \* \* \* \*

UNITED STATES PATENT AND TRADEMARK OFFICE
CERTIFICATE OF CORRECTION

PATENT NO. : 6,248,919 B1
DATED : June 19, 2001
INVENTOR(S) : Todd S. McDermott et al.

It is certified that error appears in the above-identified patent and that said Letters Patent is hereby corrected as shown below:

Title page,
Item [57], ABSTRACT, replace "the preparation of preperation of farnesyltransferase" with -- the preparation of farnesyltransferase --.

Signed and Sealed this

Seventh Day of May, 2002

Attest:

Attesting Officer

JAMES E. ROGAN
Director of the United States Patent and Trademark Office